United States Patent [19]

Seifert et al.

[11] 4,214,105

[45] * Jul. 22, 1980

[54] PROCESS FOR THE HYDROXYLATION OF PHENOL

[75] Inventors: Hermann Seifert, Cologne; Helmut Waldmann; Wulf Schwerdtel, both of Leverkusen; Wolfgang Swodenk, Odenthal-Gloebusch, all of Fed. Rep. of Germany

[73] Assignee: Bayer Aktiengesellschaft, Leverkusen, Fed. Rep. of Germany

[ * ] Notice: The portion of the term of this patent subsequent to Oct. 11, 1994, has been disclaimed.

[21] Appl. No.: 942,717

[22] Filed: Sep. 15, 1978

Related U.S. Application Data

[63] Continuation of Ser. No. 731,889, Oct. 13, 1976, which is a continuation of Ser. No. 554,048, Feb. 28, 1975, Pat. No. 4,053,523.

[30] Foreign Application Priority Data

Mar. 6, 1974 [DE] Fed. Rep. of Germany ....... 2410742

[51] Int. Cl.$^2$ ................... C07C 37/00; C07C 39/08
[52] U.S. Cl. ................................. 568/771; 568/803
[58] Field of Search ................ 568/971, 741, 803, 771

[56] References Cited

U.S. PATENT DOCUMENTS

| | | | |
|---|---|---|---|
| 3,849,502 | 11/1974 | Bourdin et al. | 568/771 |
| 3,993,673 | 11/1976 | McMullen | 260/348.5 L |
| 4,053,523 | 10/1977 | Seifert et al. | 568/771 |

*Primary Examiner*—Werren B. Lone
*Attorney, Agent, or Firm*—Sprung, Felfe, Horn, Lynch & Kramer

[57] ABSTRACT

A process for the production of pyrocatechol and hydroquinone by the hydroxylation of phenol in the nucleus with hydrogen peroxide, wherein phenol is reacted at the start of the reaction with substantially anhydrous hydrogen peroxide and wherein the reaction is carried out in the presence of a strong acid.

14 Claims, No Drawings

PROCESS FOR THE HYDROXYLATION OF PHENOL

This is a continuation, of application Ser. No. 731,889 filed Oct. 13, 1976, which is a continuation of application Ser. No. 554,048, filed Feb. 28, 1975 now U.S. Pat. No. 4,053,523.

This invention relates to a process for the production of pyrocatechol and hydroquinone by the hydroxylation of phenol in the nucleus with hydrogen peroxide.

It is known that phenol can be hydroxylated in the nucleus with aqueous hydrogen peroxide in the presence of catalytic quantities of a strong acid (DAS No. 2,064,497). The initial concentration of water in the reaction mixture, which is not regarded as critical, is less than 20% and preferably less than 10%. According to DAS No. 2,064,497, yields of around 70.3% pyrocatechol and hydroquinone, based on the hydrogen peroxide used, are obtained by using a 20-fold molar excess of the phenol, based on the quantity of peroxide, and working with hydrogen peroxide having a water content of about 5% (Example 1 of DAS No. 2,064,497). In cases where hydrogen peroxide with a water content of 56% is used (Example 4), the yield of pyrocatechol and hydroquinone is reduced to 63% under the same reaction conditions, whilst the reaction time is increased from 30 minutes to 3 hours. According to DAS No. 2,064,497, a reduction in the excess of phenol from 20 mols to 10 mols, based on 1 mol of hydrogen peroxide, reduces the yield to 60% under otherwise the same reaction conditions (Example 7 of DAS No. 2,064,497).

The use of high concentrations of hydrogen peroxide involves the danger of explosions and, for this reason, necessitates elaborate and expensive safety precautions in the case of a process intended for working on a commercial scale. According to Winnacker-Kuchler, Chemische Technologie, Vol. 1, page 561 (1969), the concentration limit at which aqueous hydrogen peroxide solutions are capable of being detonated amounts to 90%. Since the presence of organic compounds reduces the concentration limit to 70% (R. Powell "Hydrogen Peroxide Manufacture," page 184 (1968), the working conditions of DAS No. 2,064,497 always involve the danger of explosions.

According to German Pat. No. 1,543,830, this difficulty can be obviated by carrying out the hydroxylation of aromatic compounds in the nucleus with hydrogen peroxide in the presence of boric acid or boric acid derivatives, and subsequently hydrolysing the resulting boric acid esters of the hydroxylated aromatic compounds, the hydrogen peroxide being introduced into the reaction in the form of a dilute, non-aqueous solution. One of the disadvantages of using boric acid derivatives is that the boric acid derivatives of the required products are formed from the aromatic compounds to be hydroxylated and have to be subsequently hydrolysed in a further process stage.

A process for hydroxylating phenol in the nucleus with hydrogen peroxide in the presence of a strong acid has now been found, being distinguished by the fact that, at the beginning of the reaction, hydroxylation is carried out with substantially anhydrous hydrogen peroxide.

The phenol used for the process according to the invention should have as low a water content as possible. It is possible to use commercial-grade phenol which should contain no more than 0.1% of water.

Thus, according to the invention, the hydrogen peroxide used for the process, is in the form of substantially anhydrous non-aqueous solution. The concentration of the hydrogen peroxide in the solvent may be adjusted in such a way that there is no danger of explosion.

The hydrogen peroxide used for the process according to the invention may be dissolved in an further anhydrous solvent. Examples of suitable solvents include aliphatic ethers or alkyl esters such as diethyl ether, diisopropyl ether, diisoamyl ether or isoamyl acetate, preferably isoamyl acetate.

These solutions may contain up to 6% of hydrogen peroxide.

Solvents which allow a higher concentration of hydrogen peroxide are the esters and N-alkyl amides of phosphoric acid, phosphonic acid and phosphinic acid, such as for example tri-n-propyl phosphate, tri-n-butyl phosphate, tri-n-octyl phosphate, tri-2-ethyl hexyl phosphate, hexamethyl phosphoric acid triamide, methanophosphonic acid dimethyl ester, $\beta$-carbomethoxy ethanophosphonic acid methyl ester and methanophosphonic acid dimethyl amide; preferred phosphororganic solvents are methane phosphonate and triisooctyl phosphate.

A particularly suitable solvent for anhydrous hydrogen peroxide solutions is N-methyl pyrrolidone, in which up to 30% of the hydrogen peroxide is dissolved.

It is particularly advantageous and simple to use an anhydrous solution of hydrogen peroxide in the product to be hydroxylated, the phenol, for the process according to the invention.

It is also particularly advantageous and simple to prepare an anhydrous solution of hydrogen peroxide in phenol by distilling off the hydrogen peroxide and the phenol together from an anhydrous solvent whose boiling point is higher than that of the phenol and the hydrogen peroxide. Basically, any organic solvents which are chemically inert under the reaction conditions and which boil at higher temperatures than the phenol and the hydrogen peroxide, are suitable for use as non-aqueous solvents for hydrogen peroxide in this advantageous embodiment of the process according to the invention. The difference in boiling point between the reactants and the solvent preferably amounts to 50° C. Examples of suitable solvents are tri-n-octyl phosphate, tri-[(2-ethyl)-hexyl]-phosphate, hexamethyl phosphoric acid triamide, $\beta$-carbomethoxy ethanophosphonic acid butyl ester, tricyclohexyl phosphate and $\beta$-carbohydroxy ethanophosphonic acid methyl ester. Triisooctyl phosphate and $\beta$-carbomethoxy ethanophosphonic acid dibutyl ester are preferably used.

A 5 to 30% solution and preferably a 10 to 25% solution of hydrogen peroxide in an anhydrous organic solvent is used for the advantageous embodiment of the process according to the invention described above.

To prepare the anhydrous hydrogen peroxide solution in the phenol intended for hydroxylation by common distillation from the higher boiling solvent, the phenol and the non-aqueous hydrogen peroxide solution may be mixed, the order in which the components are added during mixing being basically of an arbitrary nature. However, it is preferred to introduce vapours of the phenol to be hydroxylated into the non-aqueous solution of hydrogen peroxide in an inert, higher boiling solven and to react the vapour mixture of phenol and hydrogen peroxide which distils over before or after condensation by means of a catalytic quantity of a strong acid. The common distillation of hydrogen peroxide and phenol is advantageously carried out in a distillation apparatus equipped with a sump receiver, column, condenser and reflux divider. It is particularly advisable to introduce the hydrogen peroxide solution near the head of the column and the phenol near the sump of the column, so that optimum charging of the vapours with hydrogen peroxide on the one hand, and optimum evaporation of the hydrogen peroxide from the solvent on the other hand, are obtained in accordance with the countercurrent principle.

On account of the thermal instability of hydrogen peroxide, the pressure prevailing in the distillation apparatus during the distillation of hydrogen peroxide with phenol is best selected in such a way that the temperature of the distillation sump is between 100° and 20° C. and preferably between 80° and 50° C. The vacuum required for this purpose is generally in the range of from 0.1 to 500 Torr and preferably in the range of from 5 to 200 Torr. The vapours distilling over, which consist of phenol and hydrogen peroxide, generally have hydrogen peroxide concentrations of from 0.5 to 15%. It is particularly simple by this process to prepare an approximately 15% anhydrous solution of hydrogen peroxide in the phenol. Solutions of hydrogen peroxide in phenol are not explosive and are easy to handle in this concentration range. By suitably selecting the quantitative ratios, the recycle ratio prevailing during distillation and, above all, the hydrogen peroxide concentration of the starting solution, it is possible to prepare solutions of hydrogen peroxide in phenol with as low a concentration as required.

Since phenol is used in a large excess for the process according to the invention, it is possible to adjust hydrogen peroxide concentrations of from 0.5 to 5% and preferably from 2.5 to 3.0% in the phenol. The phenol is used in an excess of from 3 to 20 mols, preferably from 10 to 15 mols, per mol of hydrogen peroxide.

Any strong acids which are inert under the reaction conditions may be used as the acids which catalyse hydroxylation of the phenol. It is possible, for example, to use sulphuric acid, sulphuric acid in admixture with phosphoric acid, perchloric acid, nitric acid, trifluoromethane sulphonic acid, perfluorobutane sulphonic acid, fluorinated acid ion exchangers of the sulphonated polymeric fluorine-substituted hydrocarbon type, fluorosulphonic acid or fluorosulphonic acid in admixture with antimony pentafluoride.

The quantity of strong acid may vary within wide limits. The acid is generally used in a quantity of from 0.001 to 2 mols and preferably in a quantity of from 0.1 to 0.5 mol per mol of hydrogen peroxide.

It is known that, in reactions with hydrogen peroxide, decomposition catalysts may either be excluded or inactivated by suitable complex formers. Examples of decomposition catalysts for hydrogen peroxide include copper, cobalt, vanadium, manganese, chromium and iron salts. As already known, suitable complex formers are phosphates or partially esterified acids of phosphorus. The neutral esters or the N-alkyl amides of phosphoric acid, phosphonic acid and phosphinic acid are particularly suitable, so that there is no need for additional stabilisation in cases where hydrogen peroxide is used in esters or alkyl amides of phosphoric acid, phosphonic acid or phosphinic acid for the hydroxylation of phenol in accordance with the invention. Where other solvents for the hydrogen peroxide or the solutions of hydrogen peroxide in the phenol to be hydroxylated are used, it is best to add stabilisers, preferably esters or N-alkyl amides of phosphoric acid, phosphoric acid or phosphinic acid. Examples of suitable stabilisers are methanophosphonic acid esters, triisooctyl phosphate, $\beta$-carbomethoxy methanophosphonate and hexamethyl phosphoric acid triamide.

The quantity of stabilisers may vary within wide limits. The stabiliser is generally used in quantities of from 0.01 to 1 mol and preferably in a quantity of from 0.1 to 0.5 mol per mol of hydrogen peroxide.

The reaction temperature applied in the process according to the invention is preferably in the range of from 20° to 150° C. and especially in the range of from 30° to 100° C. The pressure is not critical to the reaction. In principle, the reaction may even be carried out under excess pressure or in vacuo. The reaction components may be completely or partly in the gas phase. In order to dissipate the heat of reaction, the reaction vessel may be cooled with a suitable medium. In order to attain the exact reaction temperature required, the pressure prevailing in the reaction vessel is best selected in such a way that the reaction mixture just boils.

The reaction time is governed by temperature, by the molar ratio and concentration of the reactants, by the type of solvent and by the acid concentration. The velocity of the reaction is at its highest where the reaction is carried out with a high acid concentration in the absence of a solvent. In general, the reaction conditions are selected in such a way that the reaction takes place at such a velocity that more than 99% of the hydrogen peroxide has reacted after 0.5 to 3 hours and preferably after 1 to 2 hours.

The reaction mixture is worked up, for example, by neutralising the acid and subjecting the reaction mixture to fractional distillation in vacuo. Insoluble constituents of the reaction mixture, for example fluorinated or sulphonated resins, may be filtered off after the reaction. The reaction mixture may also be worked up by extraction or by a combination of extraction and distillation processes.

The phenol used in excess may be reused for the reaction, optionally after purification.

The process according to the invention is eminently suitable for the continuous production of pyrocatechol and hydroquinone, because all the unreacted reactants and auxiliary substances may be recycled without any losses and because all the stages of the process can be carried out on a commercial scale with improved yields and free from any danger of explosion. Pyrocatechol and hydroquinone are used widely as photographic developers and antioxidants (Kirk-Othmer, Encyclopedia of Chem. Technology, Vol 11, 1966).

EXAMPLE 1

(a) Preparation of an anhydrous solution of hydrogen peroxide in phenol 500 g of phenol are introduced into a distillation apparatus which is fitted with a 50 cm long Vigreux column, the condenser and receiver of which are thermostatically controlled. The phenol is then distilled off at 16 Torr with a reflux ratio of 1:1, the temperature at the head of the Vigreux column being 75° C. After the distillation rate has become constant under these conditions (19.5 g of phenol in 15 minutes), the phenol which has collected in the receiver is run off, and 1.5 g/minute of an 8.42% anhydrous solution of hydrogen peroxide in triisooctyl phosphate are introduced into the column from a dropping funnel. After 35 minutes, 49.8 g of an 8.64% anhydrous solution of hydrogen peroxide in phenol are removed from the thermostatically controlled receiver.

(b) Hydroxylation of phenol 21.1 g of an anhydrous 7.85% solution of $H_2O_2$ in phenol (this corresponds to 1.65 g of $H_2O_2=48.7$ mMol) heated to 45° C. are added dropwise over a period of 3 minutes at 50° C. to a stirred mixture of 69.2 g (0.735 mol) of phenol and 1.3 g (13.26 mMol) of 100% sulphuric acid. The mixture undergoes a spontaneous increase in temperature to 62° C. The mixture is then left to cool to 50° C. and is stirred at that temperature.

After 37 minutes, the $H_2O_2$ conversion amounts to 92.2% and, after 60 minutes, no more hydrogen peroxide can be detected. After this 60 minutes, the yield of pyrocatechol amounts to 2.97 g (27 mMol) and the yield of hydroquinone to 1.63 g (14.75 mMol), which corresponds to a yield for both diphenols of 86.1%, based on the $H_2O_2$ used.

EXAMPLE 2

A mixture of 11 g (0.117 mol) of phenol, 2.3 g of 100% $H_2SO_4$ and 5 g (40.2 mMol) of methanophosphonic acid dimethyl ester is heated with stirring to 40° C. After this temperature has been reached, 30 g of an anhydrous 5.15% solution of $H_2O_2$ in phenol (=1.55 g of $H_2O_2$, 45.6 mMol), heated to 45° C., prepared in accordance with Example 1(a), are added dropwise over a period of 10 minutes.

The temperature rises to 78° C. After 20 minutes, the $H_2O_2$ conversion amounts to 95.2%. The mixture is stirred for a further 30 minutes at 55° C. in order to complete the conversion of hydrogen peroxide. Thereafter the mixture contains 2.83 g (25.7 mMol) of pyrocatechol and 1.22 g (11.1 mMol) of hydroquinone. This corresponds to a yield of 80.7%, based on the hydrogen peroxide used.

EXAMPLE 3

11 g (0.117 mol) of phenol are heated with stirring to 65° C. 5.7 g (38 mMol) of trifluoromethane sulphonic acid and 5 g (40.2 mMol) of methanophosphonic acid dimethyl ester are then successively added. This is followed by the dropwise addition of 30 g of an anhydrous 5.15% solution of $H_2O_2$ in phenol (=1.55 g of $H_2O_2$, 45.6 mMol), heated to 45° C., prepared in accordance with Example 1 (a), in such a way that the temperature of the reaction mixture can be kept at 70° C. After 45 minutes no more $H_2O_2$ can be detected. Thereafter the mixture is found by gas chromatographic analysis to contain 2.94 g (26.7 mMol) of pyrocatechol and 1.06 g (9.6 mMol) of hydroquinone, which corresponds to a total yield of the diphenols of 79.6%, based on the $H_2O_2$ used.

EXAMPLE 4

137.9 g (1.3 mols) of phenol are heated with stirring to 50° C. This is followed by the addition of 16.2 g of a perfluorinated exchanger resin containing sulphonic acid groups, after which 50 g of an anhydrous, 10.8% solution of $H_2O_2$ in phenol (=5.4 g of $H_2O_2$, 0.159 mol), heated to 45° C., prepared in accordance with Example 1(a), are added dropwise in such a way that the temperature rises to 75° C. in 5 minutes. The drip rate is then regulated in such a way that the temperature can be kept at 75° C. After the $H_2O_2$-containing phenolic solution has been added, the mixture is stirred for a further 30 minutes at the aforementioned temperature. The mixture is then found to contain 10.3 g (93.6 mMol) of pyrocatechol and 4.12 g (37.4 mMol) of hydroquinone. This corresponds to a total yield of diphenols of 82.4%, based on the hydrogen peroxide used.

EXAMPLE 5

1 g (10 mMol) of fluorosulphonic acid and 2.5 g of triisooctyl phosphate are added to 22.25 g (0.237 mol) of phenol. The mixture is heated with stirring to 70° C., followed by the dropwise addition of 50 g of an anhydrous 3.7% solution of $H_2O_2$ in phenol (=1.85 g of $H_2O_2$, 54.4 mMol) heated to 45° C., prepared in accordance with Example 1 (a), in such a way that the temperature can be kept at 85° C. After the peroxide-containing solution has been added, the mixture is stirred for 25 minutes at 85° C. The mixture has a residual peroxide content of 0.16 g, which corresponds to an $H_2O_2$ conversion of 91.4%. The mixture is also found to contain 3.16 g (28.7 mMol) of pyrocatechol and 1.62 g (14.7 mMol) of hydroquinone. Based on the $H_2O_2$ reacted, this corresponds to a yield of diphenols of 87.2%.

EXAMPLE 6

15.1 g of an anhydrous 8.03% solution of $H_2O_2$ in phenol (=1.21 g of $H_2O_2$; 35.6 mMol) prepared in accordance with Example 1(a) and preheated to 55° C., are diluted with 46.4 g (0.493 mol) of phenol. 0.9 g (9.18 mMol) of 100% sulphuric acid and 1.0 g (8.4 mMol) of methanophosphonic acid dimethyl ester are then added to the stirred mixture. An increase in temperature to 63° C. is observed. After stirring for another hour at 55° C., the mixture is found to contain 2.21 g (20.1 mMol) of pyrocatechol and 1.29 g (11.7 mMol) of hydroquinone. Yield of diphenols: 89.3%, based on the $H_2O_2$ used.

EXAMPLE 7

56.5 g (0.6 mol) of phenol are heated to 43° C. 9.5 of an anhydrous 21.5% solution of hydrogen peroxide in methanophosphonic acid dimethyl ester (=2.04 g of $H_2O_2$, 60 mMol) are added to the stirred melt. This is followed by the introduction of 2.5 g (25.5 mMol) of 100% sulphuric acid. The mixture then undergoes a spontaneous increase in temperature to 87° C. It is left to cool to 60° C. and stirred for a further 25 minutes at that temperature. Thereafter the hydrogen peroxide conversion amounts to 91.8%. The mixture contains 3.65 g (33.2 mMol) of pyrocatechol and 1.74 g (15.8 mMol) of hydroquinone, which corresponds to a yield of these diphenols of 89.0%, based on the $H_2O_2$ reacted.

EXAMPLE 8

56.5 g (0.6 mol) of phenol are introduced with stirring into 21.5 g of an anhydrous, 8.32% solution of $H_2O_2$ in triisooctyl phosphate. This is followed by the addition of 1.5 g (15 mMol) of fluorosulphonic acid, after which the temperature of the mixture rises to 93° C. After the reaction has abated, the mixture is stirred for 30 minutes at 70° C. Thereafter the reaction mixture is found to contain 3.25 g (29.5 mMol) of pyrocatechol and 1.48 g (13.4 mMol) of hydroquinone. The $H_2O_2$ conversion amounts to 97.3%. The yield of diphenols amounts to 83.8%, based on the $H_2O_2$ reacted.

What we claim is:

1. A process for preparing pyrocatechol and hydroquinone wherein phenol is reacted at the start of the reaction with substantially anhydrous hydrogen peroxide dissolved in a non-aqueous solvent in an amount of 5 to 30 weight percent, said hydrogen peroxide having been obtained by distilling off water from an aqueous solution of hydrogen peroxide while the same is in admixture with a non-aqueous organic solvent which solvent boils at a higher temperature than phenol to leave behind as the bottoms product of the distillation a substantially anhydrous hydrogen peroxide dissolved in said non-aqueous organic solvent, the reaction being carried out in the presence of a strong acid at a temperature of 20°-150° C. in a reaction mixture consisting essentially of said hydrogen peroxide, said solvent, said phenol and said strong acid and wherein pyrocataechol and hydroquinone are recovered.

2. A process as claimed in claim 1, wherein the substantially anhydrous hydrogen peroxide is used as a solution in an ester or N-alkyl amide of phosphoric acid, a phosphonic acid or a phosphinic acid.

3. A process as claimed in claim 1, wherein the substantially anhydrous hydrogen peroxide is reacted in solution in the phenol to be hydroxylated.

4. A process as claimed in claim 1, wherein from 3 to 20 mols of phenol are used per mol of hydrogen peroxide.

5. A process as claimed in claim 4, wherein from 10 to 15 mols of phenol are used per mol of hydrogen peroxide.

6. A process as claimed in claim 1, wherein the strong acid is sulphuric acid, sulphuric acid in admixture with phosphoric acid, a fluorine-substituted sulphonic acid, a fluorine-substituted sulphurised polymeric hydrocarbon, fluorosulphonic acid or fluorosulphonic acid in admixture with antimony pentafluoride.

7. A process as claimed in claim 1, wherein from 0.001 mol to 2 mols of the strong acid are used per mol of hydrogen peroxide.

8. A process as claimed in claim 7, wherein from 0.1 to 0.5 mol of the strong acid are used per mol of hydrogen peroxide.

9. A process as claimed in claim 1, wherein the reaction is carried out in the presence of a stabiliser in a quantity of from 0.01 mol to 1 mol per mol of hydrogen peroxide.

10. A process as claimed in claim 9, wherein the stabiliser is used in a quantity of from 0.1 to 0.5 mol per mol of hydrogen peroxide.

11. A process as claimed in claim 9, wherein the stabiliser is an ester or N-alkyl amide of phosphoric acid, a phosphonic acid or a phosphonic acid.

12. A process as claimed in claim 1, wherein the temperature is from 30° to 100° C.

13. A process as claimed in claim 1, wherein the reaction is carried out continuously with recycling of the unreacted reactants.

14. A process according to claim 1 wherein the hydrogen peroxide is present in the non-aqueous solvent in a concentration of 10 to 25 weight percent.

* * * * *